United States Patent [19]
Liedtke

[11] Patent Number: 5,863,941
[45] Date of Patent: Jan. 26, 1999

[54] METHOD AND COMPOSITION OF A TOPICAL TREATMENT OF INNER EAR AND LABYRINTH SYMPTOMS

[76] Inventor: Rainer K. Liedtke, Postfach 306 D-82027 Gruenwald b., Munich, Germany

[21] Appl. No.: 679,438

[22] Filed: Jul. 8, 1996

[30] Foreign Application Priority Data

Jul. 6, 1995 [DE] Germany ............ 195 24 691.8

[51] Int. Cl.[6] .................................. A01N 37/30
[52] U.S. Cl. ........................................... 514/555
[58] Field of Search ............................ 514/555

[56] References Cited

PUBLICATIONS

Embase Abstract 89002887 (1988). Norris.

*Primary Examiner*—Zohreh Fay
*Attorney, Agent, or Firm*—Oblon, Spivak, McClelland, Maier & Neustadt, P.C.

[57] ABSTRACT

Periauricularly administered topical therapy with a carrier system containing local anesthetics is a new and effective treatment of disorders of the inner ear and labyrinth, which has a low incidence of side effects. The use of this type of therapy applies especially to a non-invasive topical treatment of tinnitus, vertigo, lack of balance, and nausea.

18 Claims, No Drawings

METHOD AND COMPOSITION OF A TOPICAL TREATMENT OF INNER EAR AND LABYRINTH SYMPTOMS

BACKGROUND OF THE INVENTION

1. Field of the Invention:

The subject of this invention relates to a method and composition of a non-invasive, topical treatment and prevention of pathological symptoms of the inner ear and labyrinth, in particular of tinnitus, vertigo, lack of balance, and nausea.

2. Discussion of the Background:

It is known that in the majority of cases, persistent tinnitus and vertigo, accompanied by a lack of balance and nausea, are due to a disorder or disease of the organs of the inner ear or of the auditory nerves. Tinnitus may occur both in the low-frequency and in the high-frequency range; in the low-frequency range, it occurs especially in the presence of disorders of the auditory canal and the middle ear, in the high-frequency, mainly in the presence of disorders of the labyrinth. These persistent symptoms have an extremely negative effect on those affected. One characteristic complex of symptoms, which includes tinnitus, vertigo and lack of balance, possibly in association with nystagmus, hearing impairment and vomiting, is seen, for example, in Menière's disease. The sudden attacks of the symptoms may be attributable to vasomotor disorders of labyrinth vessels or temporary disorders of the secretion and composition of the labyrinthine liquor. Under the influence of permanent tinnitus and impaired hearing, the persons affected often become irritable, they suffer from anxiety, and, in some cases, develop considerable psychosomatic problems as this illness proceeds.

The therapeutic methods used so far to treat these problems are not sufficiently effective. If it is not possible to identify an underlying disease, only symptomatic measures, such as stimulus deprivation, rest and pharmacological sedation, can be taken. The pharmacological principle frequently used for this purpose is the orally administered dimenhydrinate which has a sedative effect. Scopolamine, a parasympatholytic agent, may also be used; however, this agent is primarily used to treat the pathophysiologically associated phenomenon of motion-induced nausea, i.e., kinetosis, which develops on exposure to externally moving objects. This sickness is also known as motion or sea sickness and is associated with vegetative phenomena, mainly with nausea. In systemic therapy, scopolamine is also administered by transdermal route (Y. W. Chien, Novel Drug Delivery Systems, Drugs and the Pharmaceutical Sciences, Vol. 14, 1982, Marcel Decker, New York), which, when compared to the intramuscular administration of scopolamine, results in a lower and more uniform blood concentration in the body. In spite of this, however, the typical undesirable side effects of scopolamine, in particular, impaired vision, very dry mouth, changes in the ability to concentrate, and somnolence, are observed. The undesirable side effect mentioned last is, among other things, also present after an oral administration of dimenhydrinate which is also used to treat kinetoses but which is less effective. Thus, overall, the administration of scopolamine as a therapeutic principle is very restricted indeed.

In contrast, the appropriate use of local anesthetics in low doses represents a more effective pharmacological approach. A systemic administration, however, is generally possible by means of injection which as such is undesirable and which, in addition, cannot be used due to the fact that it poses the risk of a systemic overdose with serious cardiac side effects. A direct administration by injection or liquid infusion of local anesthetics to the labyrinthine apparatus of the inner ear itself is technically practically impossible; furthermore, this would carry the risk of ototoxic effects.

The pharmacological mechanism of action of local amide and ester anesthetics, e.g., amide-type lidocaine, is to inhibit the rapid sodium ion influx into the fibers of the nerves. In this manner, these anesthetics block the conduction of impulses of the nerve path, which basically includes all regional nerve fibers. Due to their morphology, however, the thinner sensory fibers are more sensitive than motor fibers, which makes it possible to differentiate between various effects. It is also known that intravenous injections of higher doses of lidocaine (T. Gejrot, Atl. Lokalanästhesie [Atlas of Local Anesthesia], pp. 151–152, Thieme, Stuttgart 1970) as well as a blockage of the ganglion cervicothoracicum with procaine have positive effects on the symptoms of Menière's disease, although these persist only for a limited period of time.

So far, a non-invasive method and composition for the treatment and prevention of pathological symptoms of the inner ear or labyrinth using a topical carrier system has neither been carried out nor described.

The use of topical carrier systems for drug delivery has been reported (see, for example, U.S. Pat. No. 4,765,986 and European Patent No. 0,205,974).

It is known that medicinal effects can be obtained with medicinal plasters or so-called therapeutic plaster systems, designated lately as transdermal therapeutic systems. At present, this type of system is used in connection with the drug scopolamine for kinetosis, nitroglycerine for coronary heart disease and clonidine for hypertension, as well as for transdermally administered estrogens.

Such plaster systems entail diffusion units in which the medications are released by diffusion at controlled rates from a mechanically fixed drug reservoir, usually tissue tolerant polymers. The systems used are currently divided into membrane systems, i.e., membrane plaster and matrix systems. In the membrane systems the drug, after release from the carrier substance, must permeate a membrane, which serves as a control element for the constant absorption rate. Thereby, it is possible to attain a release characteristic, which approximately corresponds to pharmacokinetics of zero order. In matrix systems, the drug stored in depot form diffuses directly from the polymer matrix into the skin.

However, a non-invasive method and composition for the treatment and prevention of pathological symptoms of the inner ear or labyrinth with a periauricularly administered topical carrier system has neither been carried out nor described.

SUMMARY OF THE INVENTION

The first object of this invention is to provide a therapeutic and preventative method and composition for pathological symptoms of the inner ear or labyrinth using a periauricularly administered topical carrier system.

This object is achieved by attaching a periauricularly administered topical carrier system, which contains a therapeutic or preventative dose of a local anesthetic, and a carrier substance, to the intact skin of the periauricular region and by releasing the local anesthetic into the periauricular skin region below the carrier system.

A second object of this invention provides for new indications, such as the treatment of tinnitus, vertigo, lack of balance, kinetoses and nausea, to be treated by a periauricularly administered topical carrier system which contains a local anesthetic.

A third object of this invention provides for the prevention of tinnitus, vertigo, lack of balance, kinetoses and nausea by a periauricularly administered topical carrier system which contains a local anesthetic.

DETAILED DESCRIPTION OF THE PREFERRED EMBODIMENTS

To improve the efficacy and tolerability of the periauricularly administered treatment, one embodiment of this invention is to provide a therapeutically and preventatively effective method and composition with a periauricularly administered topical carrier system having a local anesthetic and a carrier substance. The carrier system provides for topical delivery of the local anesthetic.

The local anesthetic is not particularly limited and may include any local anesthetics known in the art (see, for example, those listed in the Merck Index, 11th ed., 1989 herein incorporated by reference). Preferably, the local anesthetics include amide- or ester-type anesthetics. More preferably, the local anesthetics include lidocaine, tetracaine, bupivacaine, prilocaine, mepivacaine, procaine and benzocaine. The local anesthetics are present in the carrier substance in a range of concentrations from 0.5% to 40% by weight of the carrier substance; preferably 0.5%–30% by weight of the carrier substance, more preferably 0.5%–20% by weight of the carrier substance, most preferably 0.5%–10% by weight of the carrier substance.

To further improve the efficacy and compatibility of the treatment, another embodiment of this invention provides for at least two; preferably at least three, more preferably four or more local anesthetics with different pharmacokinetics with respect to the pathological symptoms of the inner ear or labyrinth to be combined in the periauricularly administered topical carrier system, with the individual local anesthetics being present in concentrations such that the overall concentration of the local anesthetics in the carrier substance does not exceed 40% by weight of the carrier substance; preferably 30% by weight of the carrier substance, more preferably 20% by weight of the carrier substance, and most preferably up to 10% by weight of the carrier substance.

So far, a treatment of pathological symptoms of the inner ear and labyrinth by means of a carrier system with periauricularly administered local anesthetics has neither been carried out nor described. One advantage that may be obtained from this invention results from the fact that the novel pharmacological and technical combination makes it possible for the first time to treat troublesome symptoms of the inner ear and the labyrinthine organ, for which so far no adequate therapy or preventative method and composition existed, using a non-invasive topical carrier system.

The topical treatment with local anesthetics in a carrier system which is applied to the periauricular region makes it possible to therapeutically influence terminally and functionally interlocking nerve paths in a locally targeted and persistent manner.

Furthermore, since the periauricular region has a good cutaneous absorptive capacity, any dose may be administered; low topical doses are preferred. Systemic risks are avoided since local anesthetics, e.g., lidocaine, are believed to predominantly metabolized in the course of slow cutaneous absorption so that little or no systemic concentrations of the active substances are measured.

The treatment can be controlled by the administration of any dose; preferably small doses, it has a persistent effect and, if required, it can be interrupted by removing the carrier system.

Preferably the therapeutically effective amount in the carrier comprises, in the case of, e.g., the local anaesthetic Lidocaine, a range of 10 mg to 50 mg, which is delivered to the intact skin over a span of 12 to 36 hours, at a rate in the range of 0.05–1 mg/cm$^2$ per hour.

Overall, the periauricularly administered topical treatment also has fewer systemic side effects than systemic therapies, such as diphenhydramine or scopolamine, since the active ingredient is believed not to be distributed throughout the body and since, in addition, local anesthetics are believed to be readily tolerated by the local tissues.

Topical carrier systems, and means of their development, are generally known to those of skill in the art. The carrier system of this invention may additionally contain solvents, inert agents, binders stabilizers, anti-oxidants, adhesives and backing materials. The carried system of this invention may additionally contain lubricants and emollients. The carrier system may be in the form of a single or multilayer film or sponge form.

The topical delivery system is not particularly limited and may include at least one each of the following: a backing membrane, a reservoir containing the local anesthetic or anesthetics, a microporous rate-controlling membrane, a hypoallergenic skin contact adhesive, a priming reservoir containing the local anesthetics or anesthetics, and a release or peel-off liner. Alternatively, the local anesthetic is contained in a solid carrier substance, which may be in any shape, which may melt at physiological body temperature, whereby the carrier substance may be affixed, to the bottom side of a porous and flexible synthetic material of approximately the same size and shape and the two joined parts are located in a housing, closed on top and open towards the skin side, which may be attached to the skin.

It is also possible to utilize non-homogeneously dissolving local anesthetics which are absorbed in the carrier substance in pharmaceutical technical depot form in order to provide for delayed release.

The carrier substance may include two or more layers having varying melting behavior that may be applied on top of each other in order to attain a varying successive absorption rate of the same or different local anesthetics.

The carrier substance may be distributed in the pores of the whole synthetic material in order to better retain the full flexibility of the synthetic material.

The synthetic material is not particularly limited but may be provided on its top side with a mechanical barrier layer in order to obtain a better mechanical separation between carrier substance and housing.

The synthetic material may preferably be made of polyurethane foam of the ether type or of the ester type in order to attain particularly favorable physical properties together with a physiological indifference or tolerance.

The carrier substances of solid fats/adeps solidus or mixtures of various solid fats may be preferably introduced into the pores of a synthetic material of polyurethane foam of the ether type or ester type, in order to obtain particularly favorable physical and biopharmaceutical properties together with a good physiological tolerance.

Carrier substances of gelatin or mixtures of gelatin and solid fats are preferably introduced into the pores of a synthetic material or polyurethane foam of the ether type or ester type, in order to obtain particularly favorable physical and biopharmaceutical properties, together with a good physiological tolerance. However, other suitable carrier substances meeting the above requirements may also be used. Additionally, medium chain-length partial glycerides or mixtures of partial glycerides may be introduced into the carrier substance in order to improve the release of lipophile drugs and to affect a regulation of the physical and biopharmaceutical properties of the carrier substance. Also, hydrophilic auxiliary materials may be introduced into the carrier substance in order to improve the release of hydrophilic local anesthetics from the carrier substance.

Alternatively, a one-sided self-adhesive plastic foil in connection with a one-sided self-adhesive foam ring with closed pores is used, whereby the carrier substance is joined to the bottom side of the plastic foil and placed in the opening of the foam ring, in order to obtain a better skin adhesion of the drug plaster in connection with a sufficient occlusion effect as well as a better protection of the carrier substance against thermal and mechanical influences.

The effects obtained with the successively melting carrier substance disk are comparable to the external application of liquid or viscous preparations, such as salves and sprays, or the internal use of stomach gels or suppositories. However, contrary to the application of salves and sprays, there is preferably no drying of the carrier substance due to evaporation and thus no reduction of the dissolution conditions. Because of its cover, the topical carrier system rather creates a moist chamber, which is believed to improve the penetration of the local anesthetic by increasing the hydration of the arid stratum corneum.

As it is possible to produce for each local anesthetic specific galenically optimal carrier substances, depending on its physico-chemical properties, the system has a constant basic configuration that is versatile and technologically simple. Contrary to the dermal application of salves, gels and sprays, the system preferably delivers exact dosages. There is preferably no danger of contamination or loss of medication by outside influences.

Preferably no mechanical components are present, such as membranes or adhesive foil, applied between the carrier substance and the skin, so that irritation by friction is reduced or eliminated. The bottom surface of carrier substance may be present as a liquid phase, which favors the distribution of the local anesthetic and thus produces a surface area increase into the micro topography of the skin, similar to an application of salve.

As the production of the carrier system and carrier substance, e.g. by simple molding or pressing, as in the production of suppositories, is less costly than the production of exactly dosed polymer matrices or membrane systems, it is also possible to keep production costs low.

Furthermore, it is also possible to include into the carrier system and substance, apart from homogeneously distributed local anesthetics, pharmaceutically-technically restrained formulations, which have an independent release characteristic, so that rapid as well as delayed absorption component can be simultaneously realized in the system. Another possibility for the control of varying release characteristics is the application of several carrier substances with varying melting behavior.

Due to the partial penetration of the carrier substance into the pores of the flexible elements, a firm contact between the two components is preferred, so that, even with possible damage to the carrier substance in the solid state, it does not separate fully or in part from the flexible element. The flexible element also assures, independent from the position of the application, a constant adhesion and thus a firm contact between the carrier system and the skin surface.

The local anesthetic release from the bottom of the carrier substance may be enhanced by the melting process induced by the skin temperature and the transfer into the skin occurs from the liquid phase of the carrier substance. As the carrier substance spreads as a liquid film, the total available complementary skin surface is covered even in its micro topography, contrary to the mechanically more inflexible systems which adhere flat and thus not fully, and also reach the deeper set integumentary system, such as sebaceous glands and sweat glands which present a considerable absorption area. Because of the direct adherence of the liquid phase of the carrier substance, the need for an additional adhesive foil in the absorption area, as is the case with mechanically fixed systems, is eliminated. The tight contact between the liquid phase of the carrier substance and the skin into the micro topographic area also simultaneously reduces the average diffusion distance. Thus, the optimal surface utilization of the available skin absorption area and the reduction of the diffusion distance also provide advantages in the diffusion conditions as compared to the mechanically fixed systems. The specific transport conditions through the skin surface for the various drugs, which are believed to occur according to the laws of the so-called 'non-ionic diffusion' are favored overall.

To ensure that the treatment is safer and can be handled more easily, another embodiment of this invention provides for the periauricularly administered topical carrier system to be available in shapes which correspond to the special morphology and anatomy of the periauricular region to which the system is attached. It should be noted that while the carrier substance and the flexible synthetic material may have any shape, they are preferably round, oval, angular, crescent-shaped, concave or convex. Additionally, the user, with or without additional aid, may cut the carrier system into appropriate shapes.

The term "adeps solidus" is a synonym for "solid fats". The term "solid fats" comprises triglycerides of saturated carbon acids having 10 to 18 carbon atoms in the chain.

The term "medium chain length partial glycerides" comprises mono- and diglycerides of saturated and/or unsaturated carbon acids having 8 to 12 carbon atoms in the chain.

The term "gelatin" comprises a hydrolysis product of ossein.

The term "polyurethane foam of the ether/ester type" comprises reaction products of polyfunctional isocyanates with polyesters or polyethers containing hydroxyl groups.

The carrier system may be used on the surface of any mammalian skin such as a dog or cat but, preferably human skin. The carrier system is attached to the skin and is charged with an appropriate amount of local anesthetic that is therapeutically or preventatively effective for the pathological symptoms of the inner ear or labyrinth such as tinnitus, vertigo, lack of balance, kinetoses and nausea. Of course, the precise amount of local anesthetic will vary depending upon the mammalian or human body weight, the nature of the drug and the nature of the treatment. However, such amounts would be known to those skilled in the art in view of the above disclosure.

As an example of a technically suitable embodiment of a periauricularly administered topical carrier system, reference is made to the descriptions of the technical carrier systems in U.S. Pat. No. 4,765,986 and in the European Patent No. 0,205,974, without, however, restricting the scope of this invention to the techniques described. Further, this application is based upon German Patent Application 195 24 691.8, filed in the German Patent Office on Jul. 6, 1995, the entire contents of which are hereby incorporated by reference.

Having now fully described this invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method for treating pathological symptoms of the inner ear and labyrinth of a mammal, comprising administering to a periauricular region thereof a topical carrier system which comprises a carrier substance and a therapeutically effective amount of a local anesthetic, said local anesthetic being present in a concentration of about 0.5% to 40% by weight of said carrier substance.

2. The method of claim 1, wherein said pathological symptoms comprise indications for the use of a periauricularly administered topical carrier system which comprises a local anesthetic.

3. The method of claim 2, wherein said indications comprise tinnitus, vertigo, lack of balance, kinetoses and nausea.

4. The method of claim 1, wherein said local anesthetic is an amide- or ester-type anesthetic.

5. The method of claim 4, wherein said amide- or ester-type anesthetic is selected from the group consisting of lidocaine, tetracaine, prilocaine, bupivacaine, mepivacaine, procaine and benzocaine, and wherein said anesthetic is present in a concentration of 0.5% to 40% by weight of said carrier substance.

6. The method of claim 1, wherein said local anesthetic comprises at least two local anesthetics, and wherein the total concentration of said at least two local anesthetics does not exceed 40% by weight of said carrier substance.

7. The method of claim 6, wherein at least one of said at least two local anesthetics is an amide- or an ester-type anesthetic selected from the group consisting of lidocaine, tetracaine, prilocaine, bupivacaine, mepivacaine, procaine and benzocaine.

8. The method of claim 1, wherein said local anesthetic comprises lidocaine, and wherein said therapeutically effective amount comprises 10–50 mg, and wherein said therapeutically effective amount is delievered to the intact skin at a rate of 0.05–1 $mg/cm^2$ per hour.

9. The method of claim 1, wherein said topical carrier system comprises a shape that may be round, oval, angular, or crescent-shaped and may be concave or convex, and wherein said carrier system may be cut by a user with or without additional aid into an appropriate shape.

10. A method for preventing pathological symptoms of the inner ear and labyrinth in a mammal, comprising administering to the periauricular region a topical carrier system which comprises a carrier substance in an effective amount of a local anesthetic, wherein said local anesthetic is present in an amount of about 0.5% to 40% by weight of said carrier substance.

11. The method of claim 1, wherein said mammal is a human.

12. The method of claim 1, wherein said local anesthetic is present in an amount of about 0.5% to 30% by weight.

13. The method of claim 12, wherein said local anesthetic is present in an amount of about 0.5 to 20% by weight.

14. The method of claim 13, wherein said local anesthetic is present in an amount of about 0.5 to 10% by weight.

15. The method of claim 10, wherein said mammal is a human.

16. The method of claim 10, wherein said local anesthetic is present in an amount of about 0.5 to 30% by weight.

17. The method of claim 16, wherein said local anesthetic is present in an amount of about 0.5 to 20% by weight.

18. The method of claim 17, wherein said local anesthetic is present in an amount of about 0.5 to 10% by weight.

* * * * *